US011275084B2

(12) United States Patent
Kavusi et al.

(10) Patent No.: US 11,275,084 B2
(45) Date of Patent: Mar. 15, 2022

(54) SUCCESSIVE SAMPLING DEVICE AND ASSOCIATED METHOD

(75) Inventors: Sam Kavusi, Menlo Park, CA (US); Daniel Roser, St. Georgen (DE); Christoph Lang, Cupertino, CA (US); AmirAli Haj Hossein Talasaz, Los Altos, CA (US)

(73) Assignees: Stanford University, Palo Alto, CA (US); Robert Bosch GmbH, Stuttgart (DE)

( * ) Notice: Subject to any disclaimer, the term of this patent is extended or adjusted under 35 U.S.C. 154(b) by 2650 days.

(21) Appl. No.: 12/688,193

(22) Filed: Jan. 15, 2010

(65) Prior Publication Data
US 2011/0177962 A1 Jul. 21, 2011

(51) Int. Cl.
*B01L 3/00* (2006.01)
*G01N 33/543* (2006.01)
*C12Q 1/6816* (2018.01)

(52) U.S. Cl.
CPC ..... *G01N 33/54366* (2013.01); *C12Q 1/6816* (2013.01); *G01N 33/54393* (2013.01); *B01L 3/5027* (2013.01)

(58) Field of Classification Search
None
See application file for complete search history.

(56) References Cited

U.S. PATENT DOCUMENTS

| 4,963,325 A | 10/1990 | Lennon et al. | |
|---|---|---|---|
| 2007/0178516 A1* | 8/2007 | Sosnowski et al. | ............... 435/6 |

FOREIGN PATENT DOCUMENTS

| CN | 101595388 A | 12/2009 |
|---|---|---|
| EP | 0378391 A2 | 7/1990 |
| EP | 0574782 A2 | 12/1993 |
| EP | 1890149 | 2/2008 |
| WO | 2008073393 A1 | 6/2008 |

OTHER PUBLICATIONS

Serpa et al (J. Chromatogaphy B 816:259-68) (Year: 2005).*
Vitha et al (Langmuir 24:1952-8) (Year: 2008).*
International Search Report in corresponding PCT Application (i.e., PCT/US2011/020934), dated Mar. 23, 2011 (4 pages).
Javanmard et al., "Electrical detection of protein biomarkers using bioactivated microfluidic Channels," Lab on a Chip, 2009, pp. 1429-1434, vol. 9, The Royal Society of Chemistry, Cambridge, UK (6 pages).
O'Connor et al., "The dependence of radioimmunoassay detection limits on antibody Affinity," Journal of Immunological Methods, 1997, pp. 181-189, vol. 208, Elsevier, Amsterdam, NL (9 pages).
Peterson et al., The effect of surface probe density on DNA hybridization, Nucleic Acids Research, 2001, pp. 5163-5168 (6 pages), vol. 29, No. 24, Oxford University Press, U.S.
Silzel et al., Mass-sensing, multianalyte microarray immunoassay with imaging detection, Clinical Chemistry, 1998, pp. 2036-2043 (8 pages), vol. 44, No. 9, American Association for Clinical Chemistry, U.S.
Srinivasan et al., An integrated digital microfluidic lab-on-a-chip for clinical diagnostics on human physiological fluids, Lab on a Chip, 2004, pp. 310-315 (6 pages), vol. 4, Royal Society of Chemistry, U.S.
Tudos et al., Trends in miniaturized total analysis systems for point-of-care testing in clinical chemistry, Lab on a Chip, 2001, pp. 83-95 (13 pages), vol. 1, The Royal Society of Chemistry, The Netherlands.
Wixforth, Acoustically Driven Programmable Microfluidics for Biological and Chemical Applications, Journal of the Association for Laboratory Automation, 2006, pp. 399-405 (7 pages), vol. 11, No. 6, Germany.
English Translation of KIPO Notice of Preliminary Rejection corresponding to Korean Patent Patent Application No. 10-2012-7021326 (5 pages).

* cited by examiner

Primary Examiner — Christopher M Gross
(74) Attorney, Agent, or Firm — Maginot, Moore & Beck LLP

(57) ABSTRACT

A method of determining a number of a solution constituent includes introducing a first number of solution constituents to a first test location, establishing a first binding environment for the introduced first number of solution constituents, creating a first residual number of solution constituents by binding a first plurality of solution constituents, establishing a second binding environment for the first residual number of solution constituents, creating a second residual number of solution constituents by binding a second plurality of solution constituents from the first residual number of solution constituents, obtaining a first signal associated with the bound first plurality of solution constituents, obtaining a second signal associated with the bound second plurality of solution constituents, and determining a second number of a constituent of interest based upon the obtained first signal and the obtained second signal.

20 Claims, 5 Drawing Sheets

SUCCESSIVE SAMPLING DEVICE AND ASSOCIATED METHOD

FIELD

This invention relates to diagnostic tests and more specifically to affinity based diagnostic tests.

BACKGROUND

Extensive scientific research in the fields of biochemistry and medicine, particularly in recent decades, have revealed the fact that a wide range of diseases and physical conditions are expressed by molecular changes in the human body. In many cases, early detection of the molecular changes can enable earlier diagnosis of the condition which significantly increases the potential for effectively treating the condition.

Many molecular changes are identified using assays for detecting and quantifying analyte molecules such as DNA, RNA or proteins. These assays are based on specific binding of the analyte molecules to capture molecules with the amount of bound analyte molecules typically being proportional to the total number of analyte molecules in the test solution. This type of detection method is described as "affinity assay" and usually begins with bringing a test solution containing the analyte to be detected or quantified into contact with a set of capture molecules (also referred to as probe spot). When the test solution is in contact with the capture molecules, a certain percentage of the analyte will bind to the capture molecules. After a sufficient amount of time, the test solution is removed and the presence (or quantity) of analyte molecules bound to the capture molecules is detected.

Typically, affinity assays are limited by the fact that each set of capture molecules usually yields only a single data point. A single data point is generally insufficient for computing an accurate result, especially when there are unknowns in the system. Such unknowns can be the presence of cross reactive molecules, molecules different from the analyte of interest which nonetheless bind to the capture molecules, thus rendering quantitative results useless and causing false positives.

Another unknown might be the ambient temperature or the density of capture molecules. By way of example, molecules are usually immobilized on a surface by capture molecules. One method of preparing a test site with capture molecules is contact printing. With contact printing, the density of the capture molecules deposited on the surface frequently varies from one batch to the next by a factor of 2. As reported by Peterson et al., "The effect of surface probe density on DNA hybridization", Nucleic Acids Research, Vol 29, No 24, pp. 5163-5168, Oxford University Press, capture molecule density strongly influences the amount of analyte binding. Accordingly, assays using capture molecules which have been contact printed rely upon cumbersome external calibration methods (such as a standard curve) to provide valid and meaningful results.

A need exists for a device and method of performing an affinity assay. A further need exists for low cost assays including multiplexed assays, protein arrays, lateral flow devices, sandwich assays, competitive assays, or bead based arrays, which provide accurate results and a method of using such arrays. A method and system for performing an affinity assay which allows the number of analytes within a test solution to be determined would be beneficial.

SUMMARY

In accordance with one embodiment, a method of determining a number of a solution constituent includes introducing a first number of solution constituents to a first test location, establishing a first binding environment for the introduced first number of solution constituents, creating a first residual number of solution constituents by binding a first plurality of solution constituents, establishing a second binding environment for the first residual number of solution constituents, creating a second residual number of solution constituents by binding a second plurality of solution constituents from the first residual number of solution constituents, obtaining a first signal associated with the bound first plurality of solution constituents, obtaining a second signal associated with the bound second plurality of solution constituents, and determining a second number of a constituent of interest based upon the obtained first signal and the obtained second signal.

In another embodiment, a method of determining the number of molecules involved in an analyte capture system includes introducing a first number of solution constituents to a first test location, creating a first residual number of solution constituents by binding a first plurality of solution constituents to a first percentage of a plurality of capture probes at the first test location, creating a second residual number of solution constituents by binding a second plurality of solution constituents from the first residual number of solution constituents to a second percentage of a plurality of capture probes at a second test location, obtaining a first signal associated with the bound first plurality of solution constituents, obtaining a second signal associated with the bound second plurality of solution constituents, and determining a second number of a molecule of interest based upon the obtained first signal and the obtained second signal.

In yet another embodiment, a successive sampling system includes a plurality of first capture probes, a plurality of second capture probes, a transport system for moving a first number of analytes of interest in a solution from a location proximate the plurality of first capture probes to a location proximate the plurality of second capture probes, a memory in which command instructions are stored, and a processor configured to execute the command instructions to obtain a first signal associated with a first plurality of bound first capture probes, obtain a second signal associated with a second plurality of bound second capture probes, and determine a first number of a constituent of interest based upon the obtained first signal and the obtained second signal.

DESCRIPTION

Figure 1:
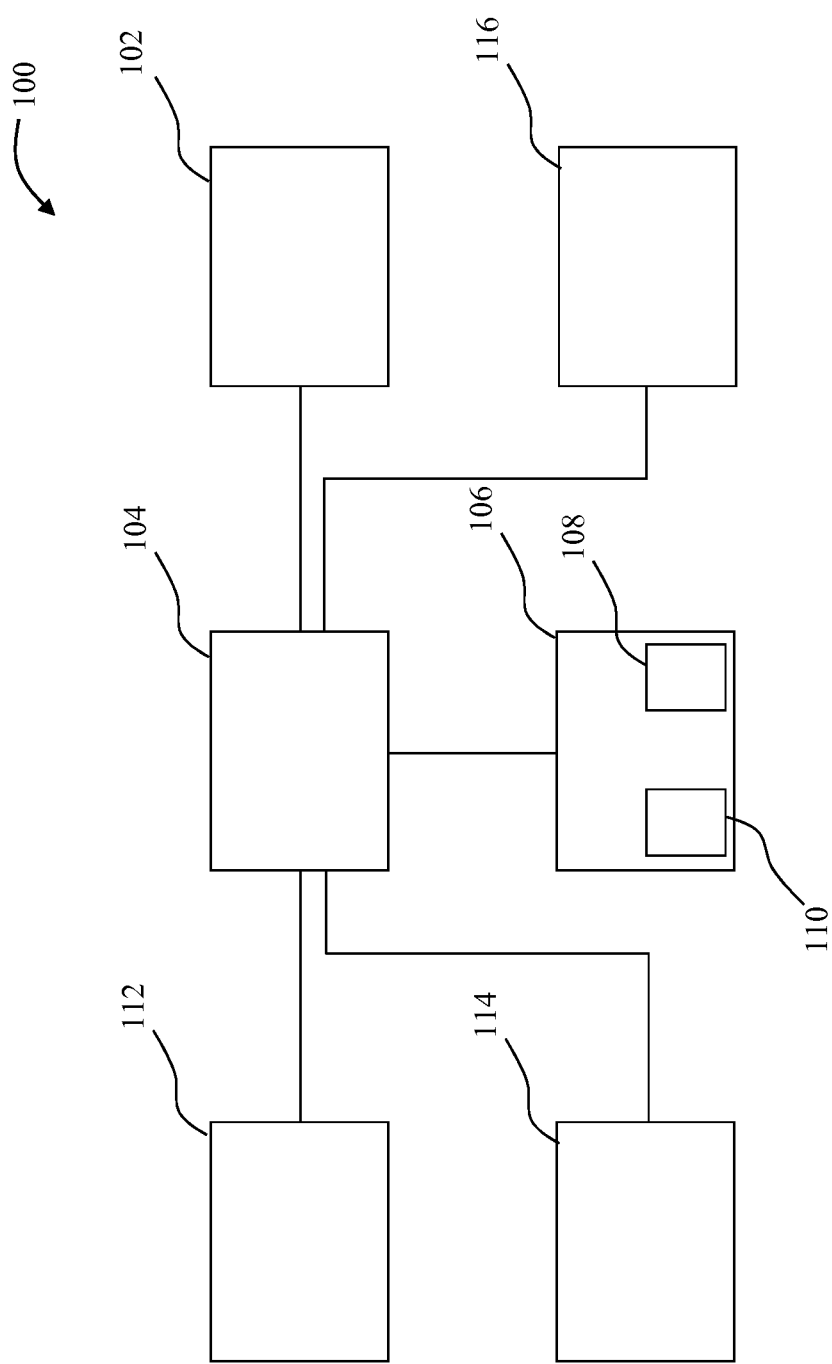
FIG. 1 depicts a successive sampling system configured to expose a single sample to successive sampling allowing determination of the number of a molecule of interest in a sample including other molecules which increase the detected signal.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A wide range of affinity assays function in accordance with the mass action law which predicts that for a given affinity constant and probe density, the percentage of analyte which will bind to the probes is constant and not a function of analyte concentration. The mass action law is expressed as:

$$\frac{b_{analyte}}{n_{analyte}} = \frac{n_{probes}k_a}{n_{probes}k_a + N_A V} = a_{analyte}$$

wherein
$b_{analyte}$ is the number of bound analyte molecules,
$n_{analyte}$ is the number of total analyte molecules in the test solution,
$n_{probes}$ is the number of total probe molecules,
$k_a$ is the association constant between the analyte molecules and the probe molecules,
$N_A$ is Avogadro's number,
V is the test solution volume, and
$a_{analyte}$ is the percentage of bound analyte.

Referring to FIG. 1, there is depicted a representation of a successive sampling system generally designated 100. The sampling system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the sampling system 100, and that allow internal information of the sampling system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components as appropriate. Association databases 110 are also located within the memory 106.

Figure 2:
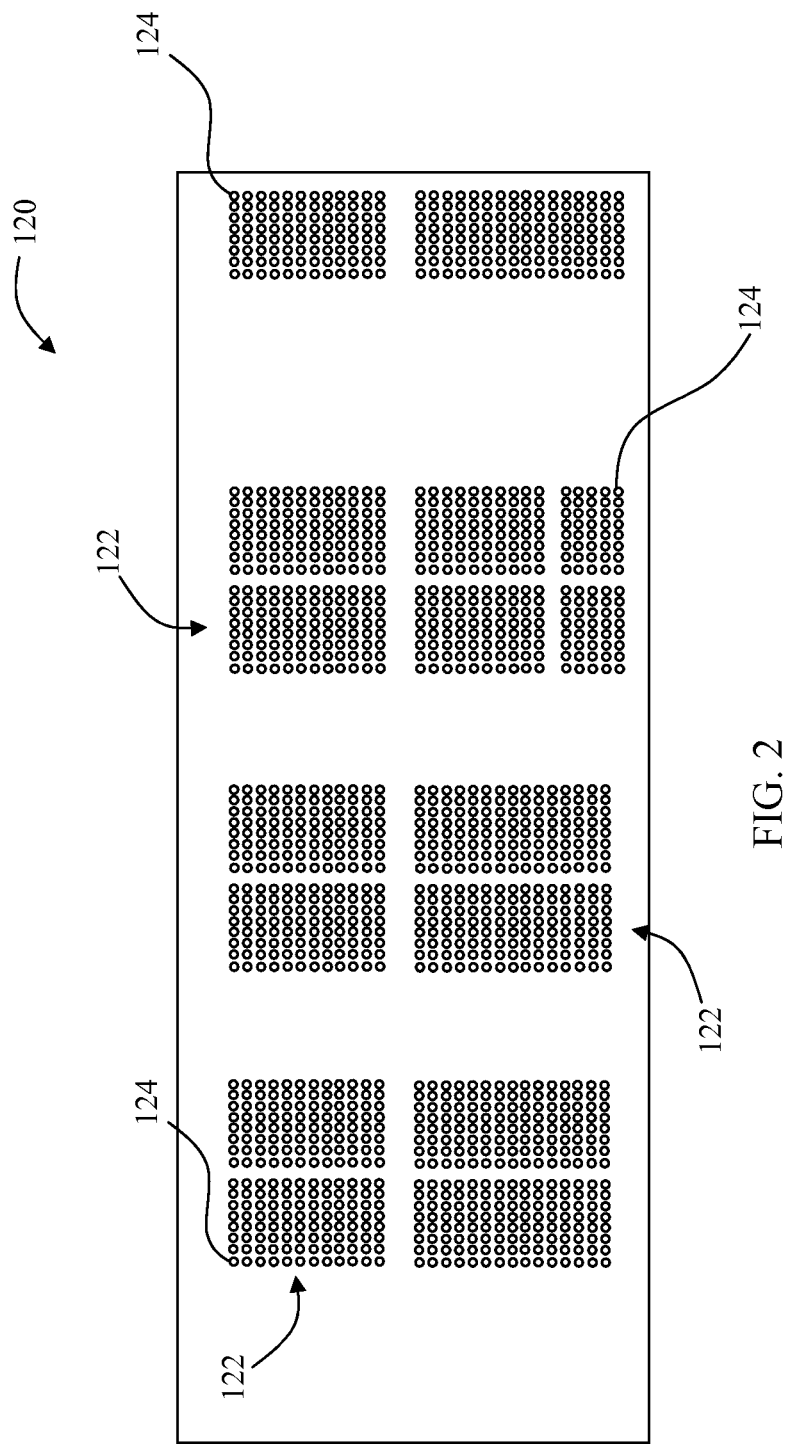
FIG. 2 depicts a platform for providing a number of different test sites in the form of a microarray.

The sampling system 100 further includes a transport control system 112 and an environment detector suite 114. The transport control system 112 is configured to move a test solution, in this example, about a microarray 120 depicted in FIG. 2. Various methods may be used to form the microarray platform 120. By way of example, U.S. Pat. No. 5,807,522 discloses a method for forming microarrays. The microarray platform 120 includes a number of different subarrays 122. The subarrays 122 include a number of test sites 124 consisting of analyte probes. The number of subarrays 122 as well as the number of test sites 124 within each of the subarrays 122 may be varied within the scope of the invention. The precise temperature of the test solution at the test sites 124 may be detected, in this embodiment, by the detector suite 114.

The system 100 further includes a sensor 116. The sensor 116 may be included in a single device along with the other components of the system 100. Alternatively, one or more of the components of the system 100 may be provided as a separate device which may be remotely located from the other components of the system 100.

The test sites 124 are prepared with a capturing agent or analyte probes effective for capturing an analyte of interest. Further details regarding the sampling system 100 are provided with reference to the procedure 130 of FIG. 3. The processor 104 executes the program instructions 108 to execute at least some of the procedure 130 of FIG. 3. In different embodiments, the procedure 130 may be modified to include more or fewer steps depending upon the specific criterion.

At block 132, an analyte of interest is identified and the $k_a$ for the analyte of interest and the probe molecules on the microarray 120 is obtained (block 134) and stored in the association database 110 (block 136). Potential sources of interference or noise likely to be present in a tested sample are then identified (block 138). The identification of signal interference may include, for example, an identification of likely or potential molecules within a sample that also have an affinity for the identified probe molecules. The $k_a$ for each source of noise with the probe molecules is then identified (block 140) and stored in one of the affinity databases 110 (block 142).

At block 144, the microarray platform 120 is prepared by depositing the desired amount of the selected probe molecules in each of the test sites 124. In alternative embodiments, a subset of the test sites 124 may be prepared with a first probe molecule while another subset of the test sites 124 may be prepared with a second probe molecule so as to allow two separate tests to be conducted within a single microarray platform 120. Additional configurations within a single microarray platform 120 may also be used. By way of example, each of the test sites within one of the subarrays 122 may be prepared with the same probe molecule while another of the subarrays 122 includes a different probe molecule. The number of test sites 124 prepared with a particular probe molecule in this embodiment is selected to be at least the same as the number of potentially interfering molecule types identified above plus the analyte of interest.

Once the microarray platform 120 is prepared, a test sample is introduced into the selected set of test sites 124 (block 146). The test sample includes a number of the analyte of interest as well as a number of interfering analytes. If not already established, the environment within each of the selected set of test sites 124 is controlled to localize the analyte of interest within the sample at a desired test site 124 or set of test sites 124 (block 148). In this example, the analyte of interest is electrically charged and the transport control system 112 is used to establish electrical forces within the test sample. The transport control system thus transports the molecules of interest within the test sample to a desired test site 124 as depicted in FIG. 4.

Figure 4:
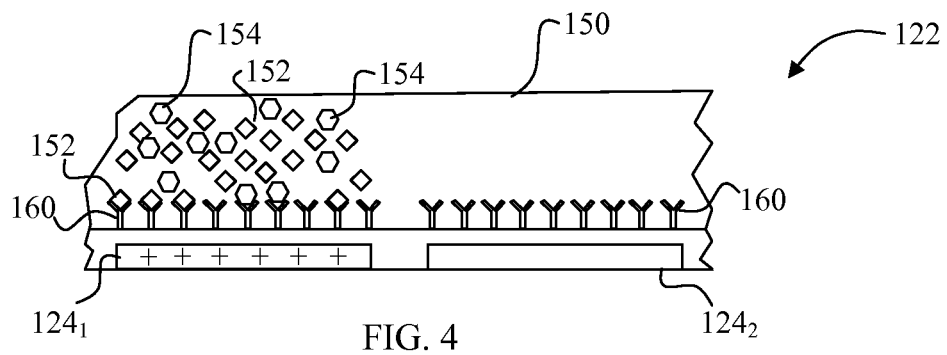
FIG. 4 depicts a schematic of a test site on an array that has been charged to transport analytes of interest within a test solution to a location adjacent a first set of capture probes.

FIG. 4 depicts a test site 124$_1$ and a test site 124$_2$ which are covered by a test sample 150. The analytes of interest 152 are negatively charged, as are the interfering analytes 154. The transport control system 112 applies a positive charge to the test site 124$_1$ which causes the negatively charged analytes of interest 152 and interfering analytes 154 to move away from the test site 124$_2$ and be concentrated above the test site 124$_1$.

The test sample 150 is then incubated for a predetermined time (block 156). During the incubation, the actual test environment within each of the selected set of test sites 124 is monitored by the environment detector suite 114 and data indicative of the established test environment is provided to the processing circuit 104 (block 158). In some embodiments, the environment may not be monitored. The environment data may include temperature, and the difference in potential between the test sites 124$_1$ and 124$_2$. During incubation, some of the analytes of interest 152 and some of the interfering analytes 154 are bound by the test probes 160 at the test site 124$_1$.

Figure 5:
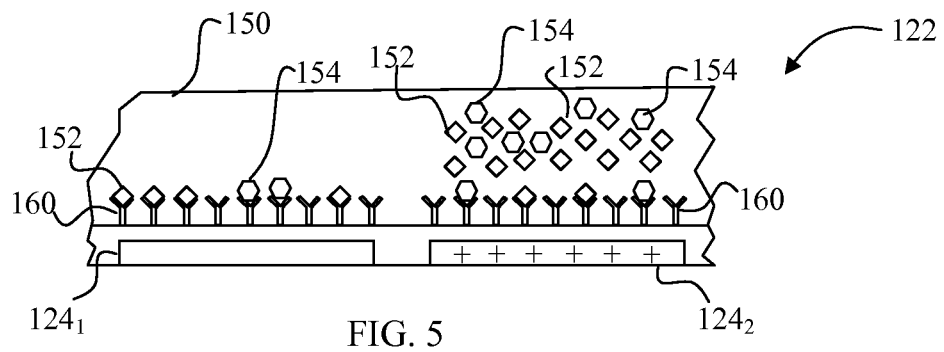
FIG. 5 depicts a schematic of a second test site on the array of FIG. 4 that has been charged to transport analytes of interest within the test solution that have not been bound at the first test site to a location adjacent a second set of capture probes.

When the sample 150 has been sufficiently incubated, the transport control system 112 applies a positive charge to the test site 124$_2$ which causes the negatively charged analytes of interest 152 and interfering analytes 154 which have not been bound to move away from the test site 124$_1$ and be concentrated above the test site 124$_2$ (block 160) as depicted in FIG. 5. The test sample 150 is then incubated for a predetermined time (block 162). During the incubation, the actual test environment within each of the selected set of test sites 124 is monitored by the environment detector suite 114 and data indicative of the established test environment is provided to the processing circuit 104 (block 164). The environment data may include temperature, and the difference in potential between the test sites 124$_1$ and 124$_2$. During incubation, some of the analytes of interest 152 and some of the interfering analytes 154 are bound by the test probes 160 at the test site 124$_2$.

When the sample 150 has been sufficiently incubated, the test sites 124 are washed (block 166) and the sensor 116 is used to detect the bound analytes of interest 152 and the bound interfering analytes 154 (block 168). A variety of sensing methods may used for quantifying analyte binding in affinity assays. Such sensing methods include luminescence, fluorescence, colorimetric, electrochemical, impedance, and magnetic readout. The sensing method preferably provides high precision indications of the number of bound probes. Based upon the signals associated with the number of bound probes in the test sites 124$_1$ and 124$_2$, the number of one or more analytes of interest within the sample is calculated by the processing circuit 104 (block 170).

Calculation of the number of one or more analytes of interest is possible since the signal obtained by the sensor 116 for a particular one of the selected set of test sites 124 is the summation of the contributors to the signal including the molecule of interest, and each of the noise sources such as interfering molecules. The relative proportion of the signal attributable to each of the contributors is dependent upon the amount of the particular contributor, the amount of the other contributors, and the relative affinity to the initially deposited capturing probes of each of the contributors. The relationship is reflected in the following equation:

$$S_1 = a_{1\text{-}1}n_{1\text{-}1} \pm a_{1\text{-}2}n_{1\text{-}2} + \ldots a_{1\text{-}x}n_{1\text{-}x}$$

wherein $S_1$ is the signal associated with the bound probes 160 in the test site 124$_1$, $a_{1\text{-}1}$ is the percentage of an analyte (1 through x) which binds to the probes 160 in the test site 124$_1$, and $n_{1\text{-}1}$ is the number in the sample of the identified analyte (1 through x) at the test site 124$_1$.

Similarly, the relationship of the signal at the test site 124$_2$ is reflected in the following equation:

$$S_2 = a_{2\text{-}1}n_{2\text{-}1} + a_{2\text{-}2}n_{2\text{-}2} + \ldots a_{2\text{-}x}n_{2\text{-}x}$$

wherein $S_2$ is the signal associated with the bound probes 160 in the test site 124$_2$, $a_{2\text{-}1}$ is the percentage of an analyte (1 through x) which binds to the probes 160 in the test site 124$_2$, and $n_{2\text{-}1}$ is the number in the sample of the identified analyte (1 through x) at the test site 124$_2$.

Since the number of the analytes at the test site 124$_2$ is equal to the original number of analytes in the test sample less the number of analytes that were bound at the test site 124$_1$, the equation for the signal at the test site 124$_2$ may be rewritten as:

$$S_2 = a_{2\text{-}1}(1-a_{1\text{-}1})n_{1\text{-}1} + a_{2\text{-}2}(1-a_{1\text{-}2})n_{1\text{-}2} + \ldots a_{2\text{-}x}(1-a_{1\text{-}x})n_{1\text{-}x}$$

The foregoing equations, for the case of two analytes, can be resolved to:

$$n_{1\text{-}1} = \frac{(S_1 - a_{1\text{-}2}S_1 - S_2)}{a_{1\text{-}1}(a_{1\text{-}1} - a_{1\text{-}2})}$$

Accordingly, because the number of probe molecules is controlled, the percentage of bound analytes can be determined for each of the analytes as a function of the affinity constant and probe density. Thus, the number of each of the analytes in the initial test solution 150 can be determined.

By way of example, the test sample 150 in one scenario includes a number of $10^6$ molecules of an analyte of interest and $10^6$ molecules of another analyte which is very similar to the analyte of interest and thus features cross reactivity. The affinity constant ($k_a$) and probe density predict that 40% of the molecules of the analyte of interest and 60% of the other analyte will bind to the capture molecules. Accordingly, 400,000 molecules of the analyte of interest and 600,000 of the other analyte molecules will be captured at test site 124$_1$ and yield a signal corresponding to 1,000,000 bound probes ($S_1$).

Upon moving the residual number of the analyte of interest and the other analyte to the test site 124$_1$ there will be 400,000 molecules of the analyte of interest and 600,000 molecules of the analyte of interest left in the test solution 150. Accordingly, after incubation, 240,000 molecules of the analyte of interest and 240,000 molecules of the other analyte will be bound at the test site 124$_2$. The signal $S_2$ will then correspond to 480,000 bound probes. Substituting the calculated binding percentages and the obtained signals in the equation above yields:

$$n_{1\text{-}1} = \frac{(1{,}000{,}000 - 0.60(1{,}000{,}000) - 480{,}000)}{0.40(0.40 - 0.60)} = 10^6$$

A multisite successive sampling system can thus be implemented on a printed circuit board, glass, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The signal estimation and the assay data can be hard coded on the CMOS chip if desired.

The transport control system 112 in the embodiment described above incorporated an electric field to move analytes within the test sample. Electric fields are useful for transporting analytes which possess a net charge when in solution such as proteins or DNA strands (see, e.g., Dalibor Hodko et al., "CMOS Electronic Microarrays in Diagnostics and Nanotechnology", CMOS Biotechnology 2007).

Electrically charged and electrically neutral analytes may also be moved in bulk using a pipette or liquid handling machine. For both electrically neutral analytes and charged analytes, other transport control systems can be used to successively sample a test solution. Technologies which may be particularly useful in a transport control system include microfluidics wherein the entire test solution is moved on chip level from one probe spot to another probe spot. Microfluidics approaches include continuous-flow microfluidics which enable the control of liquid flow through micro fabricated channels by external or internal micro pumps and valves as reported by A J Tüdős, "Trends in miniaturized total analysis systems for point-of-care testing in clinical chemistry", Lab on a Chip, 2001. A continuous flow system 200 is depicted in FIG. 6.

Figure 6:
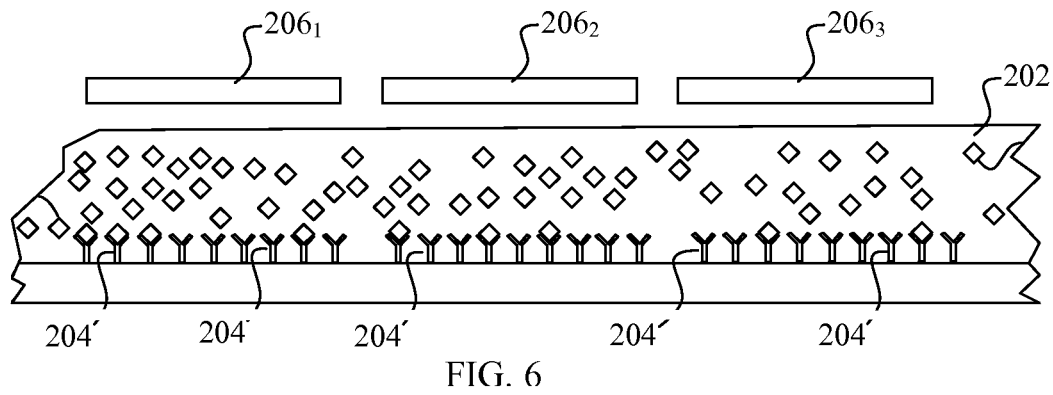
FIG. 6 depicts a schematic of a successive sampling system incorporating a lateral flow technology to capture analytes of interest from a test solution as the test solution flows past different capture probe sites.

With reference to FIG. 6, the test sample 202 is caused to flow past capture probes 204 by the continuous-flow transport system. Sensors $206_{1-3}$ are positioned along the flow path and configured to detect the number of probes 204 which have captured an analyte 208. Since the capture of analytes is a function of the number of the analytes within the test solution, the rate of capture decreases as the number of analytes within the test solution is reduced. Accordingly, the signal obtained by the sensor $206_1$ is larger than the signal produced by the sensor $206_2$. Thus, calculation of the number of analyte molecules in the embodiment of FIG. 6 is calculated in a manner similar to the calculation of the number of analyte molecules in the example set forth above.

Other technologies which may be used in a transport system include discrete microfluidics such as electrowetting on dielectric (EWOD) as reported by Vijay Srinivasan, "An integrated digital microfluidic lab-on-a-chip for clinical diagnostics on human physiological fluids", Lab Chip, 2004, 4, 310-315, or surface acoustic Waves as reported by Achim Wixforth, "Flat Fluidics: Acoustically driven planar microfluidic devices for biological and chemical application", Transducers 05. Lateral flow systems may also be incorporated wherein a liquid test solution is transferred through a porous membrane, containing several zones of reporter or capture molecules. In addition to electric fields, magnetic fields may be used to transport analytes within a solution. Analyte molecules may be labeled with a magnetic bead or charged label to assist in transportation of the analyte.

While the embodiment of FIG. 4 creates a residual number of solution constituents wherein the analytes in the residual number are those analytes that have not been bound, a residual number of solution constituents may also be generated using the analytes that have been bound such as is accomplished by the sampling system 220 of FIGS. 7-11.

Figure 8:
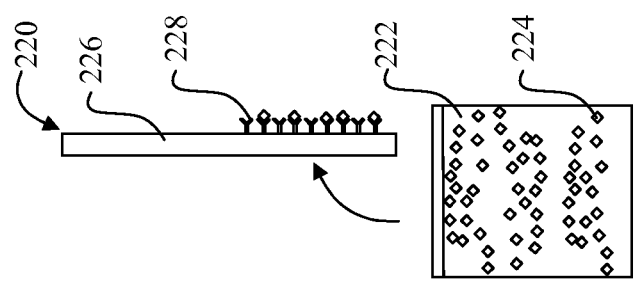
Figure 7:
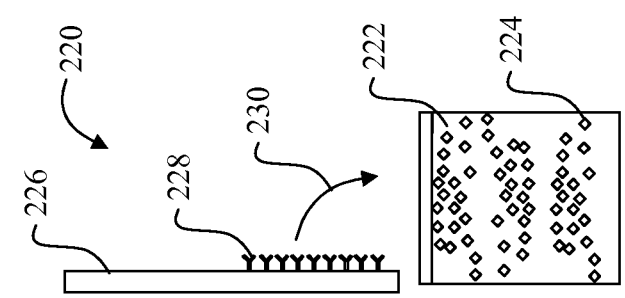

FIG. 7 depicts a test solution 222 which includes a number of analytes 224. A residual number of solution constituents is generated by placing a test strip 226 with a number of probes 228 into the solution 222 as indicated by the arrow 230. The test strip 226 is then removed with a number of analytes 224 bound to the probes 228 (FIG. 8). A first signal may be obtained from the test strip 226 indicative of the number of analytes bound to the probes 228. Prior to obtaining a signal, the test strip 226 may be washed to remove analytes which have become attached to the test strip 226 but not bound to a probe 228.

Figure 9:
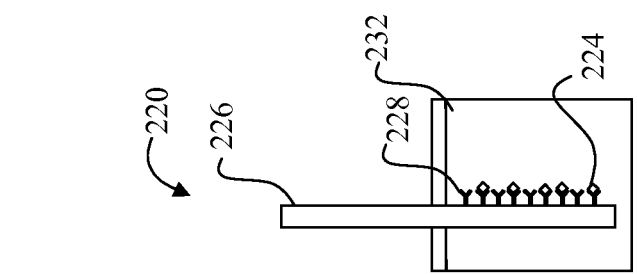

The test strip 226 is then immersed into a solution 232 shown in FIG. 9. The solution 232 may be selected to dislodge the analytes 224 from the probes 228 or the environment within the solution 232 may be controlled to break the bonds between the analytes 224 and the probes 228. The analytes 224 within the solution 232 thus form a residual number of solution constituents.

Figure 11:
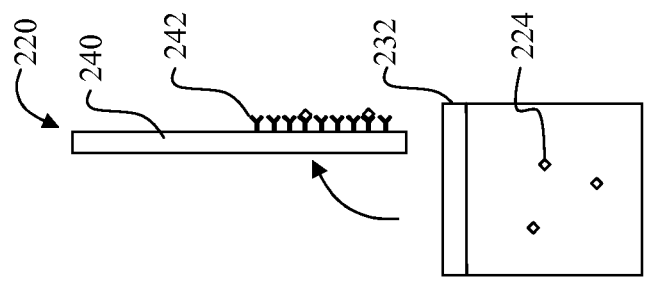
FIGS. 7-11 depict a successive sampling system wherein captured analytes of interest in a test solution are used to provide a residual number of analytes which are sampled to provide data which can be used to determine the initial number of the analytes in the test solution.
Figure 10:
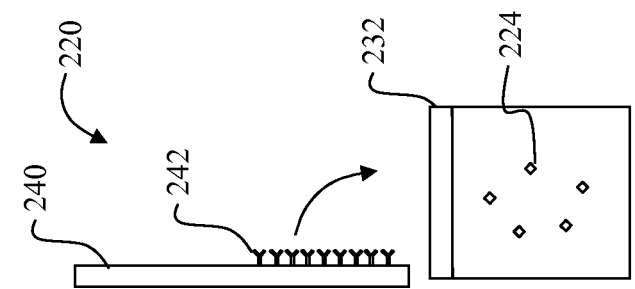

A second test strip 240 with a number of probes 242 is then exposed to the solution 232 as indicated by the arrow 244 in FIG. 10. The test strip 240 is then removed with a number of analytes 224 bound to the probes 242 (FIG. 11). A second signal may be obtained from the test strip 240 indicative of the number of analytes bound to the probes 242. Prior to obtaining a signal, the test strip 240 may be washed to remove analytes which have become attached to the test strip 240 but not bound to a probe 242. Determination of the number of analytes in the test solution 222 may be calculated using the affinity constants of the probe and the analytes along with probe density and the obtained signals.

In embodiments of the sampling system 220 wherein the environment is controlled to break the bonds between the between the analytes 224 and the probes 228, the test strip 226 may be removed after the bonds have been broken. The environment in the solution 232 may then be controlled to allow binding and the test strip 226 may be re-introduced. Binding of the analytes 224 in the solution 230 to the probes 228 would be a function of the number of analytes 224 in the solution 230. Thus, the number of analytes 224 which are bound from the solution 230 would be less than the number of analytes 224 which are bound from the solution 232.

Figure 3:
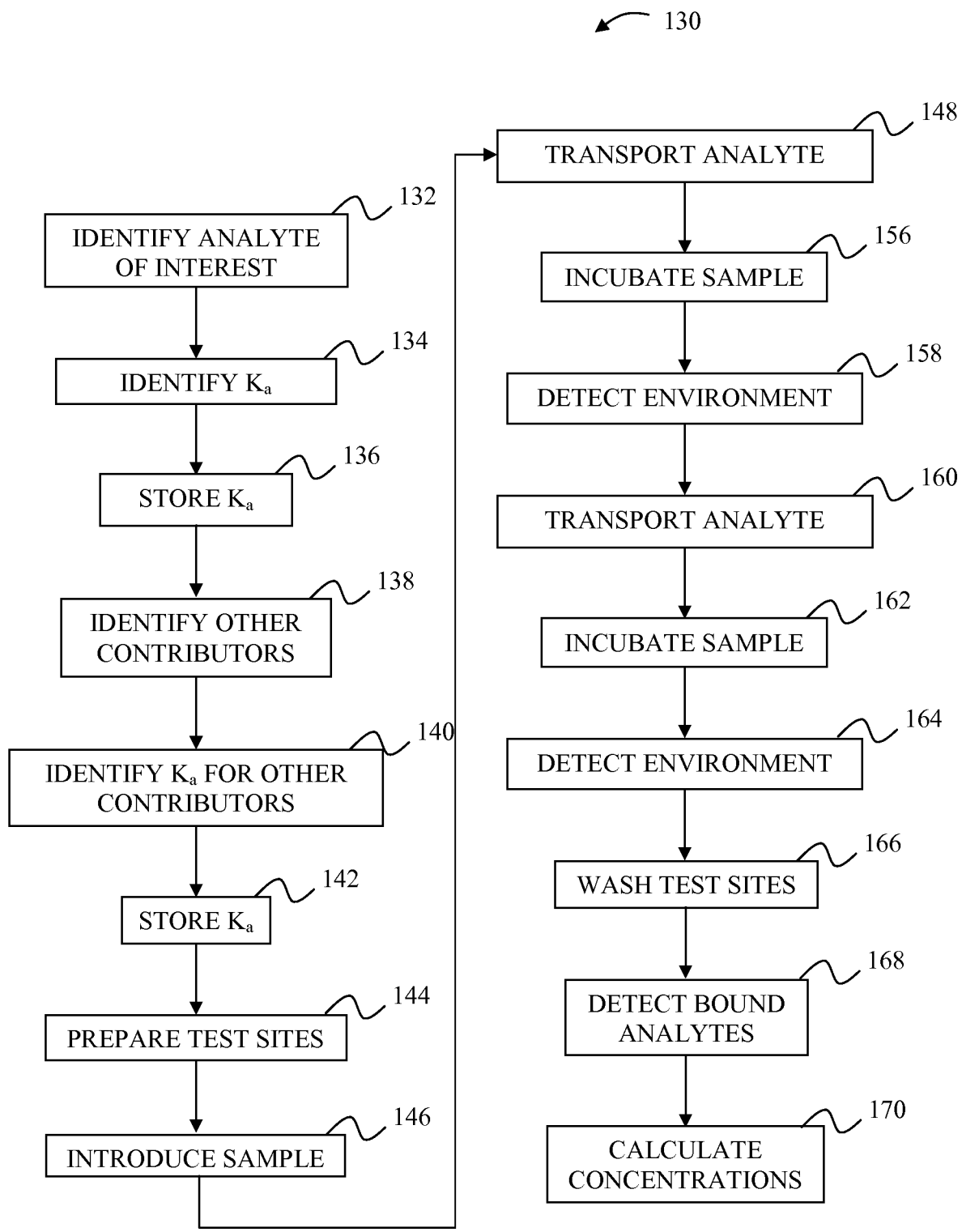
FIG. 3 depicts a procedure that can be used to successively sample a test solution at various test sites on a platform so as to expose a sample to multiple capture probe sites.

The procedure of FIG. 3 may be modified to accommodate a variety of scenarios. By way of example, the system may transport liquids rather than probes. In this scenario, a test solution is transferred into contact with a probe spot and incubated. The initial solution is then removed and a measurement of the bound analytes is obtained. A fluid without analytes or interfering constituents is then brought into contact with the probe spot and incubated, allowing some of the bound analytes to go into solution. The fluid is then removed and the probe spot is measured with the reduced number of bound analytes.

In another scenario, a solution with a number of interfering analytes that is much greater than the number of the analytes of interest can be determined even if the binding efficiency of the interfering analytes is not known. Specifically, as long as the binding efficiency is small, the number of interfering analyte molecules can be assumed to be constant even when some of the interfering analytes have been bound to capture probes. Thus, the decrease in signal between the first and second signals in successive samples is attributed solely to the change in the number of the analyte of interest. Accordingly, the number of analytes in the test solution is determined according the following formula:

$$n_{analyte} = \frac{(S_1 - S_2)}{a_{analtye}^2}$$

The procedure of FIG. 3 may further be modified to calibrate different batches of test platforms. By using a test solution with a single binding analyte, a residual number of the analyte may be obtained in a manner such as the procedure of FIG. 3. Signals associated with the bound analytes from the initial solution and from the residual solution may then be used to ascertain the number of analytes in the original solution according to the equation:

$$n_{analyte} = \frac{S_1^2}{S_1 - S_2}$$

In this equation, binding efficiency is not required. Accordingly, this equation may be used in scenarios wherein the binding efficiency is not known.

Additionally, using, e.g., the equation set forth above in paragraph 44, the signals obtained from a test solution ($S_1$) and a residual solution ($S_2$) are determined according to the following equations:

$$S_1 = a_1 n_1$$

$$S_1 = a_1^2 n_1$$

wherein $n_1 = n_{analyte}$.

Thus, for scenarios wherein the percentage of analyte molecules which bind to capture molecules is not known, the number of analytes in a solution can be determined according to the equation:

$$n_1 = \frac{S_1^2}{S_2}$$

The equation set forth above in paragraph 44 is also useful in scenarios wherein an interfering analyte is present in the solution. In this scenario, the signals obtained from a test solution ($S_1$) and a residual solution ($S_2$) are determined according to the following equations:

$$S_1 = a_1 n_1 + a_2 n_2$$

$$S_2 = a_1^2 n_1 + a_2^2 n_2$$

Thus, for scenarios wherein the percentage of analyte molecules which bind to capture molecules is not known, the number of analytes in a solution including an interfering species can be determined according to the equation:

$$n_1 = \frac{S_2 - a_2 S_1}{a_1^2 - a_1 a_2}$$

Once the number of analytes in the original solution is ascertained, the number of capture probe molecules may be determined using the mass action law described above. This approach may be modified to compensate for other unknowns affecting binding efficiencies for a particular combination of analytes and capture probes such as temperature.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A method of determining a number of a solution constituent comprising:
    determining a first percentage of a first solution constituent of interest that will be bound at a first affinity assay test location based upon a first affinity constant associated with the first affinity assay test location and a probe density of the first affinity assay test location;
    determining a second percentage of a second solution constituent that will be bound at the first affinity assay test location based upon a second affinity constant associated with the first affinity assay test location and the probe density of the first affinity assay test location;
    introducing a first number of solution constituents to the first affinity assay test location;
    creating a first residual number of solution constituents by binding with a plurality of identical probe molecules a first plurality of solution constituents at the first affinity assay test location wherein the first plurality of solution constituents includes a first portion of the first solution constituent of interest and a first portion of the second solution constituent;
    creating a second residual number of solution constituents by binding a second plurality of solution constituents from the first residual number of solution constituents wherein the second plurality of solution constituents includes a second portion of the first solution constituent of interest and a second portion of the second solution constituent;
    obtaining a first signal associated with the bound first plurality of solution constituents;
    obtaining a second signal associated with the bound second plurality of solution constituents; and
    determining a second number of the first solution constituent of interest based upon the determined first percentage, the determined second percentage, the obtained first signal and the obtained second signal, wherein the obtained first signal and the obtained second signal are used to compensate for the second solution constituent.

2. The method of claim 1, further comprising:
    transporting the first residual number of solution constituents from the first affinity assay test site to a second affinity assay test site.

3. The method of claim 2, wherein transporting the first residual number of solution constituents comprises:
    transporting a plurality of analytes bound to a respective plurality of capture probes from the first affinity assay test site to a second affinity assay test site.

4. The method of claim 3, further comprising:
    releasing the transported plurality of bound analytes from the respective plurality of capture probes.

5. The method of claim 4, wherein releasing the transported plurality of bound analytes comprises:
    releasing the transported plurality of bound analytes by modifying the temperature of the transported plurality of bound analytes.

6. The method of claim 4, wherein releasing the transported plurality of bound analytes comprises:
    releasing the transported plurality of bound analytes by exposing the transported plurality of bound analytes to a dehybridation solution.

7. The method of claim 2, wherein transporting the first residual number of solution constituents comprises:
    transporting the first residual number of solution constituents using a microfluidics technology.

8. The method of claim 2, wherein transporting the first residual number of solution constituents comprises:
   transporting the first residual number of solution constituents using a capillary flow.

9. The method of claim 2, wherein transporting the first residual number of solution constituents comprises:
   transporting the first residual number of solution constituents using magnetic beads.

10. The method of claim 2, wherein transporting the first residual number of solution constituents comprises:
    transporting the first residual number of solution constituents by modifying an electrical charge acting upon the first residual number of solution constituents.

11. The method of claim 1, wherein the first plurality of solution constituents includes a first portion of a third solution constituent and the second plurality of solution constituents includes a second portion of the third solution constituent, the method further comprising:
    creating a third residual number of solution constituents by binding a third plurality of solution constituents from the second residual number of solution constituents wherein the third plurality of solution constituents includes a third portion of the first solution constituent of interest, a third portion of the second solution constituent, and a third portion of the third solution constituent;
    obtaining a third signal associated with the bound third plurality of solution constituents; and
    determining a third number of the second solution constituent based upon the obtained first signal, the obtained second signal, and the obtained third signal.

12. The method of claim 1, wherein the second residual is created at a second affinity assay test location, and determining a second number of the first solution constituent of interest comprises determining the second number based upon the following equations:

$$S_1 = a_{1\text{-}1} n_{1\text{-}1} + a_{1\text{-}2} n_{1\text{-}2} + \ldots a_{1\text{-}x} n_{1\text{-}x}$$

$$S_2 = a_{2\text{-}1} n_{2\text{-}1} + a_{2\text{-}2} n_{2\text{-}2} + \ldots a_{2\text{-}x} n_{2\text{-}x}$$

wherein
   "$S_1$" is the first signal,
   "$S_2$" is the second signal,
   "$a_{1\text{-}1}$" is a known percentage (a) of a solution constituent (1 through x) which binds at the first affinity assay test location such that $a_{1\text{-}1}$ is the first percentage and $a_{1\text{-}2}$ is the second percentage,
   "$n_{1\text{-}1}$" is a number (n) of the solution constituent (1 through x) at the first affinity assay test location,
   "$a_{2\text{-}1}$" is a known percentage (a) of a solution constituent (1 through x) which binds at the second affinity assay test location, and
   "$n_{2\text{-}1}$" is a number (n) of the solution constituent (1 through x) at the second affinity assay test location.

13. A method of determining a number of a solution constituent comprising:
    determining a first percentage of a first solution constituent of interest that will be bound at a first affinity assay test location based upon a first affinity constant associated with the first affinity assay test location and a probe density of the first affinity assay test location;
    determining a second percentage of a second solution constituent that will be bound at the first affinity assay test location based upon a second affinity constant associated with the first affinity assay test location and the probe density of the first affinity assay test location;
    determining a third percentage of the first solution constituent of interest that will be bound at a second affinity assay test location based upon a third affinity constant associated with the second affinity assay test location and a probe density of the second affinity assay test location;
    determining a fourth percentage of the second solution constituent that will be bound at the second affinity assay test location based upon a fourth affinity constant associated with the second affinity assay test location and the probe density of the second affinity assay test location;
    providing the first affinity assay test location and the second affinity assay test location with identical probe molecules;
    introducing a first number of first and second solution constituents to the first affinity assay test location;
    creating a first residual number of first and second solution constituents by binding a first plurality of first and second solution constituents at the first affinity assay test location wherein the first plurality of first and second solution constituents includes a first portion of the first solution constituent of interest and a first portion of the second solution constituent;
    creating a second residual number of first and second solution constituents by binding a second plurality of first and second solution constituents from the first residual number of first and second solution constituents at the second affinity assay test location wherein the second plurality of first and second solution constituents includes a second portion of the first solution constituent of interest and a second portion of the second solution constituent;
    obtaining a first signal associated with the bound first plurality of first and second solution constituents;
    obtaining a second signal associated with the bound second plurality of first and second solution constituents; and
    determining a second number of the first solution constituent of interest based upon the first percentage, the second percentage, the third percentage, the fourth percentage, the obtained first signal and the obtained second signal, wherein the obtained first signal and the obtained second signal are used to compensate for the second solution constituent.

14. The method of claim 13, further comprising:
    transporting the first residual number of solution constituents from the first affinity assay test site to the second affinity assay test site by transporting a plurality of analytes bound to a respective plurality of capture probes from the first affinity assay test site to the second affinity assay test site.

15. The method of claim 14, further comprising:
    releasing the transported plurality of bound analytes from the respective plurality of capture probes.

16. The method of claim 15, wherein releasing the transported plurality of bound analytes comprises:
    releasing the transported plurality of bound analytes by modifying the temperature of the transported plurality of bound analytes.

17. The method of claim 15, wherein releasing the transported plurality of bound analytes comprises:
    releasing the transported plurality of bound analytes by exposing the transported plurality of bound analytes to a dehybridation solution.

18. The method of claim 13, further comprising:

transporting the first residual number of solution constituents from the first affinity assay test site to the second affinity assay test site by transporting the first residual number of solution constituents by modifying an electrical charge acting upon the first residual number of solution constituents.

19. The method of claim 13, wherein the first plurality of solution constituents includes a first portion of a third solution constituent and the second plurality of solution constituents includes a second portion of the third solution constituent, the method further comprising:

creating a third residual number of solution constituents by binding a third plurality of solution constituents from the second residual number of solution constituents at a third affinity assay test location with a probe molecule identical to the probe molecules at the first and second affinity assay test locations, wherein the third plurality of solution constituents includes a third portion of the first solution constituent of interest, a third portion of the second solution constituent, and a third portion of the third solution constituent;

obtaining a third signal associated with the bound third plurality of solution constituents; and determining a third number of the second solution constituent of interest based upon the obtained first signal, the obtained second signal, and the obtained third signal.

20. The method of claim 13, wherein determining a second number of the first solution constituent of interest comprises determining the second number based upon the following equations:

$$S_1 = a_{1\text{-}1} n_{1\text{-}1} + a_{1\text{-}2} n_{1\text{-}2} + \ldots a_{1\text{-}x} n_{1\text{-}x}$$

$$S_2 = a_{2\text{-}1} n_{2\text{-}1} + a_{2\text{-}2} n_{2\text{-}2} + \ldots a_{2\text{-}x} n_{2\text{-}x}$$

wherein

"$S_1$" is the first signal,

"$S_2$" is the second signal,

"$a_{1\text{-}1}$" is a known percentage (a) of a solution constituent (1 through x) which binds at the first affinity assay test location such that $a_{1\text{-}1}$ is the first percentage and $a_{1\text{-}2}$ is the second percentage, "$n_{1\text{-}1}$" is a number (n) of the solution constituent (1 through x) at the first affinity assay test location, "$a_{2\text{-}1}$" is a known percentage (a) of a solution constituent (1 through x) which binds at the second affinity assay test location such that $a_{2\text{-}1}$ is the third percentage and $a_{2\text{-}2}$ is the fourth percentage, and "$n_{2\text{-}1}$" is a number (n) of the solution constituent (1 through x) at the second affinity assay test location.

* * * * *